(12) United States Patent
Hughes (10) Patent No.: US 8,651,045 B2
(45) Date of Patent: Feb. 18, 2014

(54) DEVICE AND METHOD FOR ORIENTATING A PLURALITY OF CASSETTES FOR LABORATORY SAMPLES

(75) Inventor: Thomas Fergus Hughes, Eastbourne (GB)

(73) Assignee: Raymond A. Lamb Limited, East Sussex (GB)

( * ) Notice: Subject to any disclaimer, the term of this patent is extended or adjusted under 35 U.S.C. 154(b) by 728 days.

(21) Appl. No.: 12/514,657

(22) PCT Filed: Nov. 27, 2007

(86) PCT No.: PCT/GB2007/050716
§ 371 (c)(1),
(2), (4) Date: Nov. 6, 2009

(87) PCT Pub. No.: WO2008/068525
PCT Pub. Date: Jun. 12, 2008

(65) Prior Publication Data
US 2010/0086684 A1    Apr. 8, 2010

(30) Foreign Application Priority Data

Dec. 6, 2006   (GB) .................................. 0624392.7

(51) Int. Cl.
*B05C 5/02* (2006.01)
(52) U.S. Cl.
USPC ................... 118/300; 101/35; 347/1; 422/62; 422/64; 422/554; 422/558; 422/562
(58) Field of Classification Search
USPC .............. 118/300; 422/62, 64, 554, 558, 562; 347/1; 101/35, 44; 414/222.01, 935, 414/937, 940; 209/523, 529, 606; 53/53; 198/370.03; 141/249
See application file for complete search history.

(56) References Cited

U.S. PATENT DOCUMENTS

| 4,596,107 A * | 6/1986 | Pfleger, Sr. ......................... 53/53 |
| 5,298,425 A | 3/1994 | Kuhn et al. |
| 5,386,318 A * | 1/1995 | Kuhnert et al. ............... 359/394 |

(Continued)

FOREIGN PATENT DOCUMENTS

| DE | 44 19 500 A1 | 12/1995 |
| EP | 1 154 301 A1 | 11/2001 |

(Continued)

OTHER PUBLICATIONS

International Search Report for PCT/GB2007/050716.

*Primary Examiner* — Laura Edwards
(74) *Attorney, Agent, or Firm* — Fay Sharpe LLP (57) ABSTRACT

A device (1) is provided for orientating a plurality of laboratory sample cassettes (2) each having a marking surface (3) disposed on a main body (4) of the cassette (2). A cassette (2) is held by a clamp so that a printer can print on the marking surface (3) of the cassette (2). When the cassette (2) is released from the clamp, it is moved via a belt (13) to an opening (20) of a rotatable structure (15) in a cassette receiving position. When the cassette (2) has been received in the opening (20), the rotatable structure (15) is rotated so that the opening (20) is moved to a cassette releasing position. A rack (23) is positioned beneath the rotatable structure (15) in order to receive the cassette (2) from the rotatable structure opening (20) when the opening (20) is in its cassette releasing position. The cassette (2) is received into a rack slot (24) so that the marking surface (3) of the cassette (2) is at the top of the cassette (2). The rack (23) is then moved each time after it has received a cassette so that a successive rack slot is able to receive another cassette moved by the device (1) from the clamp and printer.

19 Claims, 4 Drawing Sheets

(56) References Cited

U.S. PATENT DOCUMENTS

| | | |
|---|---|---|
| 6,363,687 B1 | 4/2002 | Luciano et al. |
| 2003/0059281 A1* | 3/2003 | Kiene et al. ........................ 414/1 |
| 2004/0213651 A1 | 10/2004 | Malin |

FOREIGN PATENT DOCUMENTS

| | | |
|---|---|---|
| GB | 1 238 734 | 7/1971 |
| GB | 2 235 163 A | 2/1991 |
| WO | WO 97/39348 | 10/1997 |

* cited by examiner

DEVICE AND METHOD FOR ORIENTATING A PLURALITY OF CASSETTES FOR LABORATORY SAMPLES

This application is the national filing of and claims the benefit of International Patent Application No. PCT/GB 2007/050716, filed on Nov. 27, 2007 and claims the priority benefit of GB Patent Application Serial No. 0624392.7, filed Dec. 6, 2006, the subject matter of which is incorporated herein by reference.

The present invention relates to a device and method for orientating a plurality of laboratory sample cassettes each having a marking surface disposed on a main body of the cassette.

A tissue processing laboratory sample cassette, such as a biopsy cassette may have a marking or writing surface disposed generally at an angle to the main body of the cassette. A clamp is used to hold such a cassette so that its marking surface is held face down and a printer then prints on the marking surface. After printing, the cassette is ejected from the printer and is either collected in a hopper or is slid down a chute to a bench surface in a laboratory. This is repeated a number of times and a person subsequently handles the cassettes collected.

When a plurality of cassettes are printed, simply collecting them in a hopper or on a bench surface can lead to the problem of errors in their subsequent handling and the problem of the amount of time consumed with regard to having human intervention in handling the cassettes.

It is an object of the present invention to provide a device and method to alleviate the above-mentioned problems.

According to one aspect of the present invention there is provided a device for orientating a plurality of laboratory sample cassettes each having a marking surface disposed on a main body of the cassette, the device comprising:

means for moving one said cassette from an apparatus for holding said cassette and marking the marking surface of said cassette; and a rotatable structure having an opening for receiving said cassette and being rotatable so as to rotate the opening between a cassette receiving position and a cassette releasing position.

The device preferably includes a guide for guiding said cassette to the rotatable structure so that the cassette can be received in the opening when the opening is in the cassette receiving position. The device may have a base and the guide is arranged to guide said cassette so that the main body of the cassette is at an inclined angle to the base when the cassette reaches the rotatable structure.

Where the laboratory sample cassette has a marking or writing surface disposed at an angle to the main body of the cassette, the guide preferably has the main body of the cassette inclined so that the marking surface is substantially facing down.

A guard may extend at least partially around the rotatable structure for preventing a cassette received in said opening from falling out of said opening when the opening is between said cassette receiving position and said cassette releasing position.

Storage means may be provided for receiving a cassette from the rotatable structure opening when the opening is in its cassette releasing position. The storage means is preferably located below the rotatable structure. The storage means may comprise a series of openings, each opening suitable for holding one said cassette and the storage means preferably comprises a rack. Indexing means may be provided to move said storage means so that successive openings of the storage means are sequentially alignable with the opening of the rotatable structure when the opening is in its cassette releasing position.

The rotatable structure of the device may include a plurality of rotatable structure openings. The rotatable structure openings may be offset from each other. The rotatable structure openings may be angularly offset about an axis of rotation of the rotatable structure. The rotatable structure openings may be longitudinally offset along an axis of rotation of the rotatable structure.

There may be provided a laboratory sample cassette printer including a device as previously described. The printer thus is able to organise cassettes as they are printed.

According to another aspect of the present invention there is provided a method for orientating a plurality of laboratory sample cassettes each having a marking surface disposed on a main body of the cassette, the method comprising the steps of:

moving one said cassette from an apparatus for holding said cassette and marking the marking surface of said cassette into an opening in a rotatable structure; and rotating the rotatable structure so that the opening is rotated to a position to release the cassette from the structure.

The method may include rotating the rotatable structure so that the opening is rotated to a position to receive the cassette.

The cassette may be released in a manner so that the marking surface of the cassette is at the top of the cassette. Thus, when the cassette is received in a storage means such as a rack described above the marking surface is visible.

The marking surface of the cassette may be at the end of the cassette to first enter the rotatable structure opening when the cassette moves into the opening.

Embodiments of the present invention will now be described, by way of example, with reference to the accompanying schematic drawings, in which.

Referring to FIGS. 1 to 4 of the accompanying drawings, a device 1 is arranged to orientate a plurality of laboratory sample cassettes 2 and each cassette 2 has a writing or marking surface 3 disposed at an inclined angle A to the main body 4 of the cassette 2.

A clamp 5 for holding one said cassette 2 has an inclined surface 6 for holding the main body 4 of the cassette 2 at an incline and has a stop 7 at the bottom of the inclined surface 6 for the cassette 2 to rest against. The clamp 5 has a plunger 8 for holding the marking surface 3 face down so that a printer 29 can print on the marking surface 3. When the plunger 8 releases the marking surface 3, the main body 4 of the cassette 2 remains at an incline.

The device 1 has a guide 10 to one side of the clamp 5 and the guide 10 has a surface 11 disposed at an inclined angle relative to a base 12 of the device 1. The surface 11 is inclined at the same angle as the inclined surface 6 of the clamp 5 and is aligned with the clamp's inclined surface 6.

The device or eject mechanism 1 has a belt 13 for removing the cassette 2 from the clamp 5 after the clamp 5 has released the cassette 2. The belt 13 is perpendicular to, and above, the inclined surfaces 6,11. Raised blocks 14 are spaced along the outside of the belt 13 for engaging a side 9 of the main body 4 of the cassette 2.

At the bottom of the guide 10 adjacent to the clamp stop 7 is a rotatable structure or round element 15 surrounded by a cylindrical guard 16. The longitudinal axis 17 of the rotatable structure 15 and guard 16 are coincident and the axis 17 is parallel to, and beneath, the inclined guide surface 11. The guard 16 has a first opening 18 along its length inside of which is the bottom of the inclined guide surface 11 and the guard 16 has a second opening 19 along the length of the bottom of the guard 16. The guard 16 has end walls 27 which each mount an axle 28 about which the rotatable structure 15 rotates and the axles 28 are coincident with the axis 17. The rotatable structure 15 has an opening 20 or cut out or pocket just large enough to accept one said cassette 2 via the first guard opening 18. The guide 10 has a sensor 21 adjacent the first guard opening 18 to sense when a cassette 2 is aligned with the rotatable structure opening 20 when the opening is aligned with the first guard opening 18.

Beneath the second opening 19 of the guard 16 is another sensor 22. A rack 23 is also beneath the second opening 19 and has successive slots 24 or openings, each slot 24 being suitable for holding one said cassette 2. Indexing means 25 are provided to move the rack 23 so that successive slots 24 of the rack 23 are sequentially alignable with the second guard opening 19.

Figure 5:
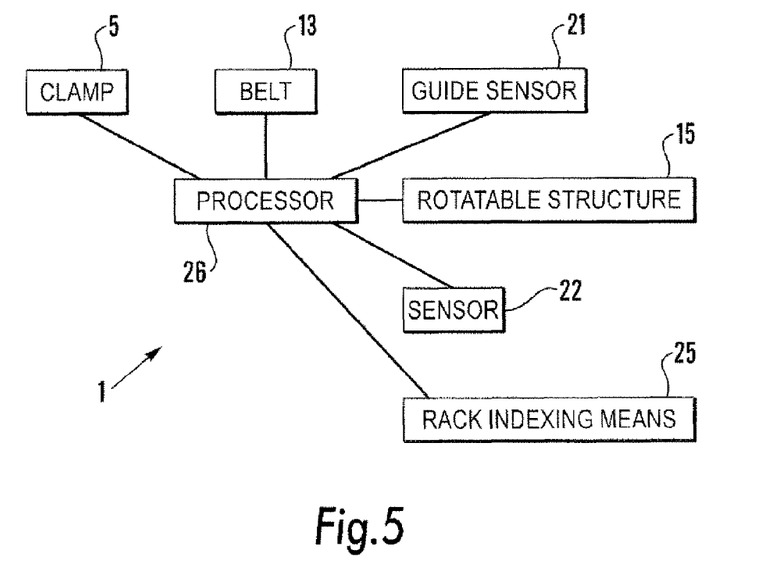
FIG. 5 is a view of the device showing a controlling processor.

Referring to FIG. 5, the device 1 has a controlling processor 26 connected to the clamp 5, the belt 13, the guide sensor 21, the rotatable structure 15, the sensor 22 beneath the guard 16, and the indexing means 25 for the rack 23.

In use, a laboratory sample cassette 2 is released by the clamp plunger 8. The controlling processor 26 causes the rotatable structure 15 to rotate until the opening 20 is aligned with the first guard opening 18. The processor 26 then actuates the belt 13 so that a block 14 on the belt 13 engages a side 9 of the main body 4 of the cassette 2. The belt block 14 pushes the cassette 2 from the inclined surface 6 of the clamp 5 and along the inclined guide surface 11 with the cassette 2 resting against the rotatable structure 15 at the bottom of the guide 10.

The clamp 5 can then receive the next cassette 2 for printing.

When the guide sensor 21 senses that the cassette 2 is aligned with the rotatable structure opening 20 (see FIG. 3) the belt 13 is stopped so that the cassette 2 slides off the guide 10 and into the opening 20 in the rotatable structure 15 via the first guard opening 18. The marking surface 3 of the cassette 2 is the first part of the cassette 2 to enter the rotatable structure opening 20. Once the cassette 2 has left the belt 13, the belt 13 can be activated again to bring the next cassette 2 from the clamp 5.

The rotatable structure 15 is then rotated until the opening 20 is aligned with the second guard opening 19 and the guard 16 prevents the cassette 2 from falling out of the opening 20 when the opening 20 is between the first and second guard openings 18,19.

Figure 1:
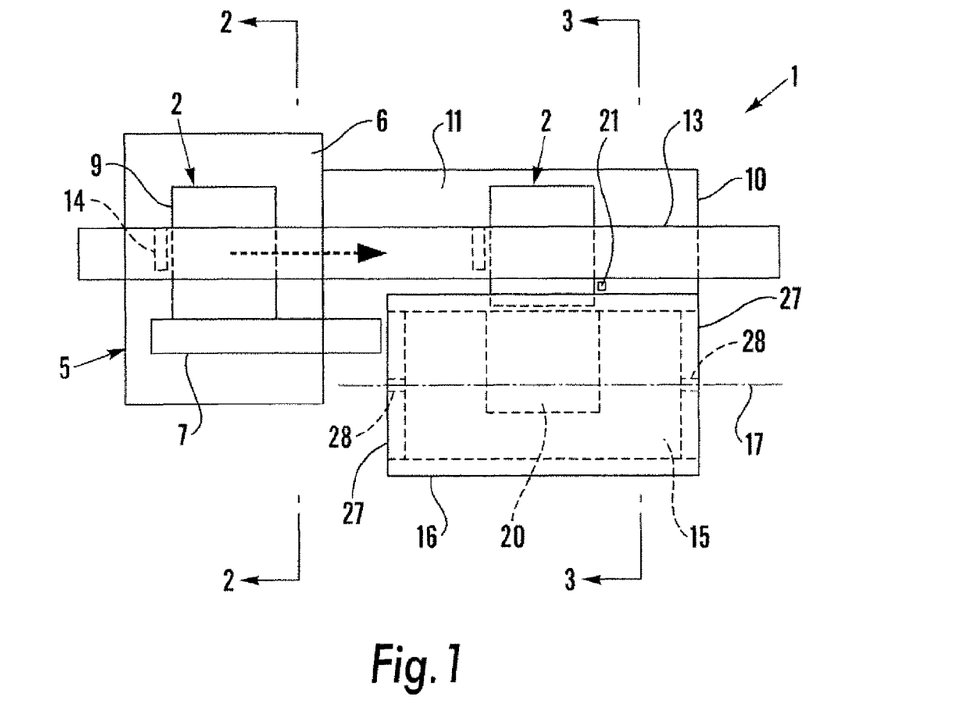
FIG. 1 is a plan view of a cassette orientating device according to one embodiment of the invention.
Figure 2:
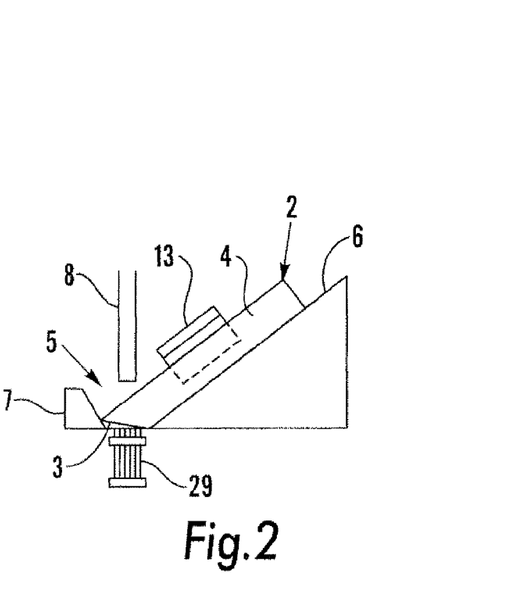
FIGS. 2 and 3 are cross-sectional views taken along lines 2-2 and 3-3, respectively, of FIG. 1.
Figure 3:
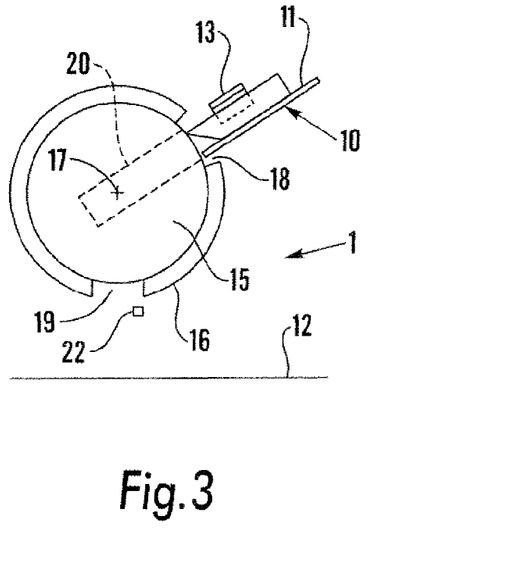
Figure 4:
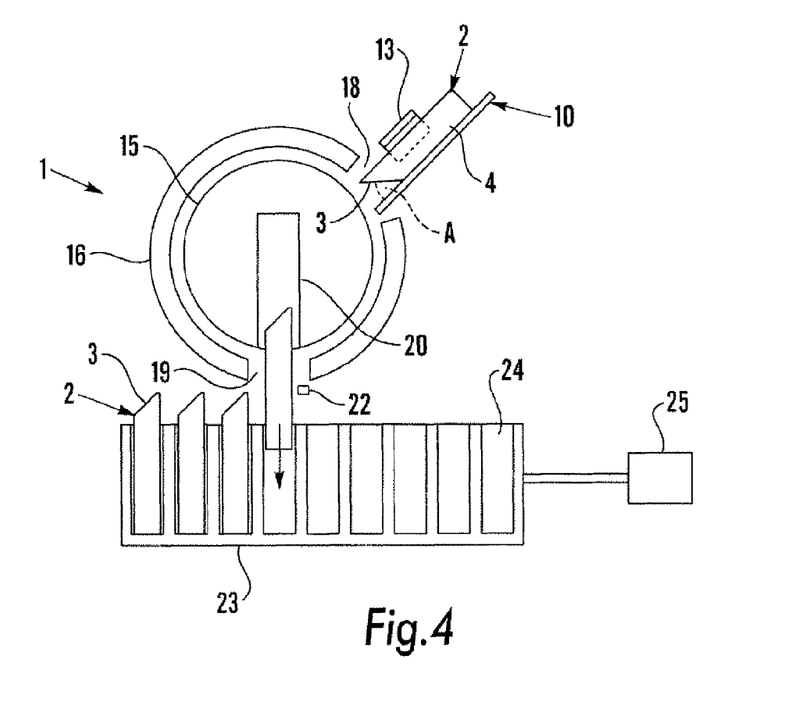
FIG. 4 is a view similar to FIG. 3 and additionally showing a rack of the device.

When the rotatable structure opening 20 reaches the second guard opening or exit point 19 the cassette 2 falls past the sensor 22 into an empty slot 24 of the rack 23 below and the marking surface 3 of the cassette 2 is at the top of the cassette 2 which protrudes above the slot 24 (see FIG. 4).

The controlling processor 26, receiving a signal from the sensor 22 that the cassette 2 has left the rotatable structure 15, causes the rotatable structure 15 to rotate until the opening 20 is aligned with the first guard opening 18. The rack 23 is also moved by the indexing means 25 so that a successive rack slot 24 is aligned with the second guard opening 19.

Thus, the device 1 collects printed cassettes 2 and orientates them so that their marking surfaces 3 are visible when the cassettes 2 are in the rack 23.

Figure 6:
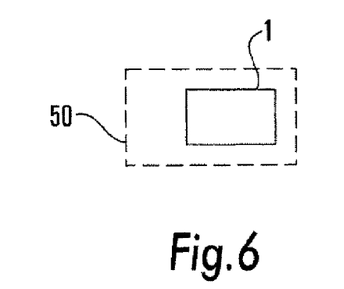
FIG. 6 is a view of a laboratory sample cassette printer including the device.

The device 1 may be included in a laboratory sample cassette printer 50 as illustrated in FIG. 6.

Figure 7:
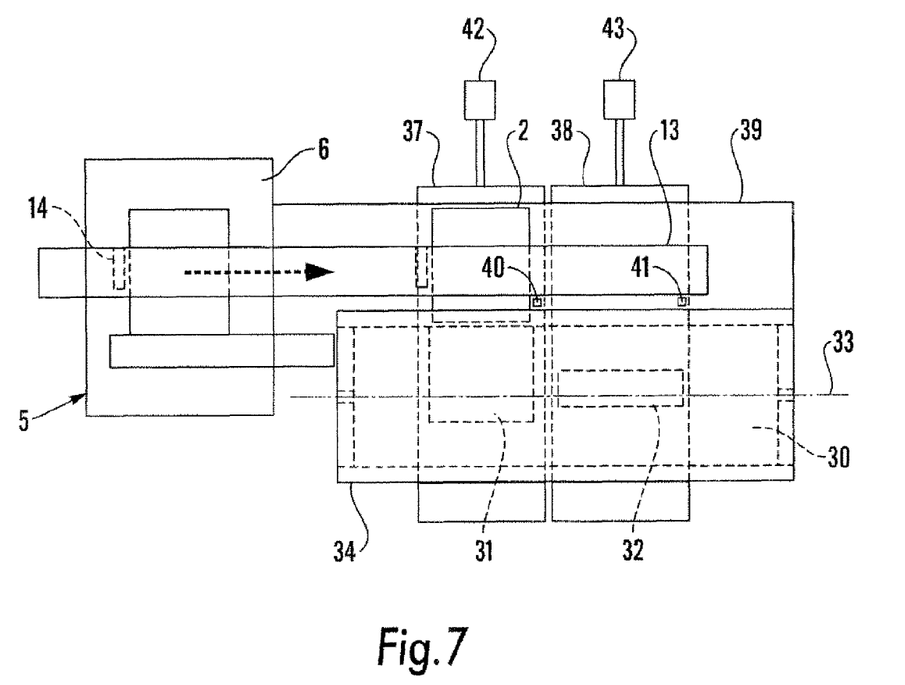
FIG. 7 is a plan view of a cassette orientating device according to another embodiment of the invention.
Figure 8:
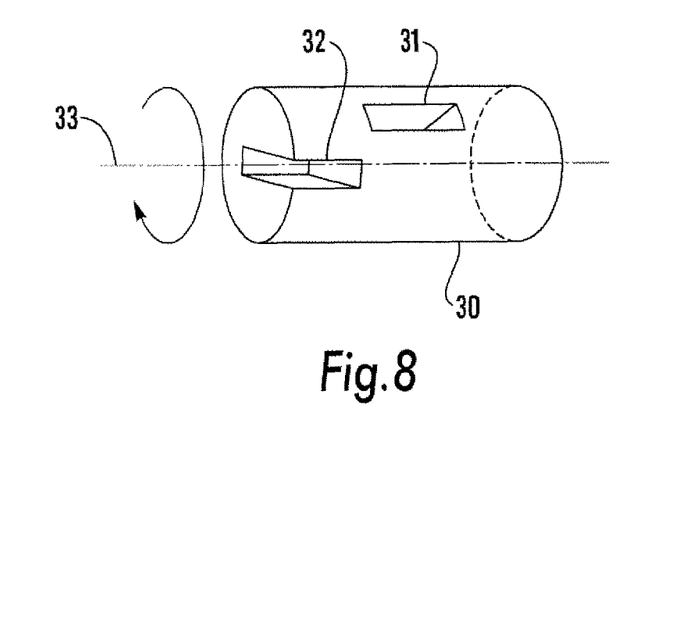
FIG. 8 is a perspective view of a part of a rotatable structure of the device of FIG. 7.
Figure 9:
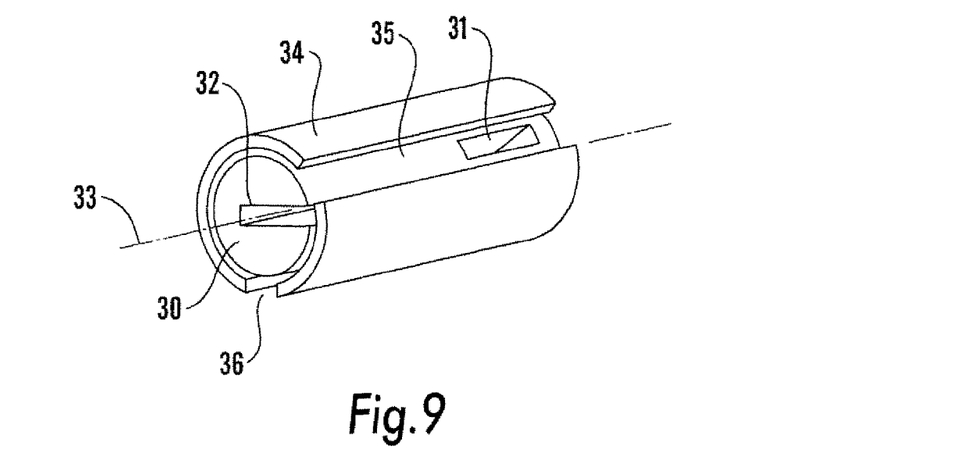
FIG. 9 is a perspective view similar to FIG. 8 and showing a guard around the rotatable structure.

A modified rotatable structure 30 is illustrated in FIGS. 7 to 9. The rotatable structure 30 has first and second openings 31,32 or cut outs or pockets. The openings 31,32 are both angularly offset about, and longitudinally offset along, the axis of rotation 33 of the rotatable structure 30. Like the first embodiment, the guard 34 has elongate first and second guard openings 35,36, along the length of the guard 34. First and second racks 37,38 are respectively positioned along the elongate second guard opening 36 so that the first rack 37 is aligned with the first rotatable structure opening 31 when the first opening 31 is aligned with the elongate second guard opening 36 and the second rack 38 is aligned with the second rotatable structure opening 32 when the second opening 32 is aligned with the elongate second guard opening 36. The guide 39 has first and second sensors 40,41, one for each opening 31,32 of the rotatable structure 30.

When the first rotatable structure opening 31 is aligned with the first guard opening 35 and the first guide sensor 40 senses that a cassette 2 being moved by the belt 13 is aligned with the first rotatable structure opening 31, the belt 13 is stopped so that the cassette 2 can slide into the first rotatable structure opening 31. The rotatable structure 30 is then rotated so as to deliver the cassette 2 to the first rack 37 below.

When the second rotatable structure opening 32 is aligned with the first guard opening 35 and the second guide sensor 41 senses that a cassette 2 being moved by the belt 13 is aligned with the second rotatable structure opening 32, the belt 13 is stopped so that the cassette 2 can slide into the second rotatable structure opening 32. The rotatable structure 30 is then rotated so as to deliver the cassette 2 to the second rack 38 below.

Each rack 37,38 is driven separately by respective indexing means 42,43 to enable sorting between the racks.

Whilst particular embodiments have been described, it will be understood that various modifications may be made without departing from the scope of the invention. The rotatable structure may be rotated until the or one said rotatable structure opening is aligned with the first guard opening only after the cassette has reached the first guard opening.

Although sensors have been described for controlling movement of the belt, the belt position may be monitored through a feed back position. Where the belt is driven by a stepper motor, belt movement may be controlled by the number of steps taken by the stepper motor.

The controlling processor may be the processor for controlling the printer for printing the cassettes.

A shoot or guide may be used for collecting printed cassettes from the rotatable structure instead of a rack.

In a modification to the first embodiment, the guide may have a stop aligned with the first guard opening so that when a cassette reaches the stop the belt is stopped enabling the cassette to slide from the guide and into the rotatable structure.

The invention claimed is:

1. A device for orientating a plurality of laboratory sample cassettes each having a marking surface disposed on a main body of the cassette, the device comprising:
   an apparatus for both holding said cassette and marking the marking surface of said cassette;
   a mechanism configured to move one said cassette from the apparatus for both holding said cassette and marking the marking surface of said cassette;
   a rotatable structure having an opening for receiving said cassette from said mechanism and being rotatable so as to rotate the opening between a cassette receiving position and a cassette releasing position;
   at least one sensor to effect sensing and alignment of the cassette with the rotatable structure;
   a base;
   a guide for guiding said cassette to the rotatable structure so that the cassette can be received in the opening when the opening is in the cassette receiving position, the guide being arranged to guide said cassette so that the main body of the cassette is at an inclined angle to the base when the cassette reaches the rotatable structure;
   a storage member configured to receive a cassette from the rotatable structure opening when the opening is in its cassette releasing position, the storage member including a series of openings, each opening suitable for holding one said cassette;
   an indexer configured to move said storage member so that successive openings of the storage member are sequentially alignable with the opening of the rotatable structure when the opening is in its cassette releasing position; and
   a controller to effect control in movement of the cassette through the device.

2. The device as claimed in claim 1, including a guard extending at least partially around the rotatable structure for preventing a cassette received in said opening from falling out of said opening when the opening is between said cassette receiving position and said cassette releasing position.

3. The device as claimed in claim 1, wherein the storage member includes a rack.

4. The device as claimed in claim 1, wherein the storage member is located below the rotatable structure.

5. The device as claimed in claim 1, including a plurality of rotatable structure openings.

6. The device as claimed in claim 5, wherein the rotatable structure openings are offset from each other.

7. The device as claimed in claim 6, wherein the rotatable structure openings are angularly offset about an axis of rotation of the rotatable structure.

8. The device as claimed in claim 6, wherein the rotatable structure openings are longitudinally offset along an axis of rotation of the rotatable structure.

9. A laboratory sample cassette printer including a device as claimed in claim 1.

10. A device for orientating a plurality of laboratory sample cassettes each having a marking surface disposed on a main body of the cassette, the device comprising:
    an apparatus for both holding said cassette and marking the marking surface of said cassette;
    a mechanism configured to move one said cassette from the apparatus for both holding said cassette and marking the marking surface of said cassette;
    a rotatable structure having a plurality of openings offset from each other, each opening suitable for receiving said cassette from said mechanism, the rotatable structure being rotatable so as to rotate the openings between a cassette receiving position and a cassette releasing position;
    at least one sensor to effect sensing and alignment of the cassette with the rotatable structure;
    a storage member configured to receive a cassette from the rotatable structure opening when the opening is in its cassette releasing position, the storage member including a series of openings, each opening suitable for holding one said cassette;
    an indexer configured to move said storage member so that successive openings of the storage member are sequentially alignable with the opening of the rotatable structure when the opening is in its cassette releasing position; and
    a controller to effect control in movement of the cassette through the device.

11. The device as claimed in claim 10, including a guard extending at least partially around the rotatable structure for preventing a cassette received in said opening from falling out of said opening when the opening is between said cassette receiving position and said cassette releasing position.

12. The device as claimed in claim 10, wherein the storage member includes a rack.

13. The device as claimed in claim 10, wherein the rotatable structure openings are angularly offset about an axis of rotation of the rotatable structure.

14. The device as claimed in claim 10, wherein the rotatable structure openings are longitudinally offset along an axis of rotation of the rotatable structure.

15. A laboratory sample cassette printer including a device for orientating a plurality of laboratory sample cassettes each having a marking surface disposed on a main body of the cassette, the device comprising:
    an apparatus for both holding said cassette and marking the marking surface of said cassette;
    a mechanism configured to move one said cassette from the apparatus for both holding said cassette and marking the marking surface of said cassette;
    a rotatable structure having an opening for receiving said cassette from said mechanism and being rotatable so as to rotate the opening between a cassette receiving position and a cassette releasing position;
    at least one sensor to effect sensing and alignment of the cassette with the rotatable structure;
    a storage member configured to receive a cassette from the rotatable structure opening when the opening is in its cassette releasing position, the storage member including a series of openings, each opening suitable for holding one said cassette;
    an indexer configured to move said storage member so that successive openings of the storage member are sequentially alignable with the opening of the rotatable structure when the opening is in its cassette releasing position; and
    a controller to effect control in movement of the cassette through the device.

16. The device as claimed in claim 15, including a guard extending at least partially around the rotatable structure for preventing a cassette received in said opening from falling out of said opening when the opening is between said cassette receiving position and said cassette releasing position.

17. The device as claimed in claim 15, including a plurality of rotatable structure openings.

18. The device as claimed in claim 17, wherein the rotatable structure openings are angularly offset about an axis of rotation of the rotatable structure.

19. The device as claimed in claim 17, wherein the rotatable structure openings are longitudinally offset along an axis of rotation of the rotatable structure.

* * * * *

UNITED STATES PATENT AND TRADEMARK OFFICE
CERTIFICATE OF CORRECTION

PATENT NO. : 8,651,045 B2  Page 1 of 1
APPLICATION NO. : 12/514657
DATED : February 18, 2014
INVENTOR(S) : Thomas Fergus Hughes It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 979 days.

Signed and Sealed this

Twenty-ninth Day of September, 2015

Michelle K. Lee
*Director of the United States Patent and Trademark Office*